United States Patent [19]

Wenshau et al.

[11] Patent Number: 4,918,999
[45] Date of Patent: Apr. 24, 1990

[54] SAMPLER FOR SOLID MATERIALS

[75] Inventors: Hugo Wenshau, Dallas; Grant G. Rice, Arlington, both of Tex.

[73] Assignee: Intersystems, Inc., Omaha, Nebr.

[21] Appl. No.: 345,018

[22] Filed: Apr. 28, 1989

[51] Int. Cl.$^5$ .............................................. G01N 1/20
[52] U.S. Cl. ................................................ 73/863.54
[58] Field of Search ................... 73/863.41–863.45, 73/863.51–863.57, 863.81, 863.82, 863.54

[56] References Cited

U.S. PATENT DOCUMENTS

| | | | |
|---|---|---|---|
| 1,966,712 | 7/1934 | Fisher et al. | 73/863.54 |
| 2,683,373 | 7/1954 | Gallup et al. | 73/863.53 |
| 3,076,341 | 2/1963 | Murray et al. | 73/863.53 |
| 4,054,060 | 10/1977 | Ueno et al. | 73/863.81 |
| 4,574,645 | 3/1986 | Allen et al. | 73/863.51 |

Primary Examiner—Robert R. Raevis
Attorney, Agent, or Firm—Bernard Malina

[57] ABSTRACT

A wood chip sampler is provided which is capable of extracting a repeatable and reliable sample of wood chips or similar particulate material from a product stream. The apparatus includes a sampling probe which has a slot which allows the product to enter the sampling probe. The probe is driven into the product stream with the slot in a six o'clock position, rotated through the twelve o'clock position to allow the product to enter the sampling probe, and then rotated to place the slot in a three o'clock position, and then retracted from the product stream into a housing. Once retracted, the probe is again rotated to place the slot on a six o'clock position, allowing the sampled material to be discharged by gravity into a hopper.

16 Claims, 7 Drawing Sheets

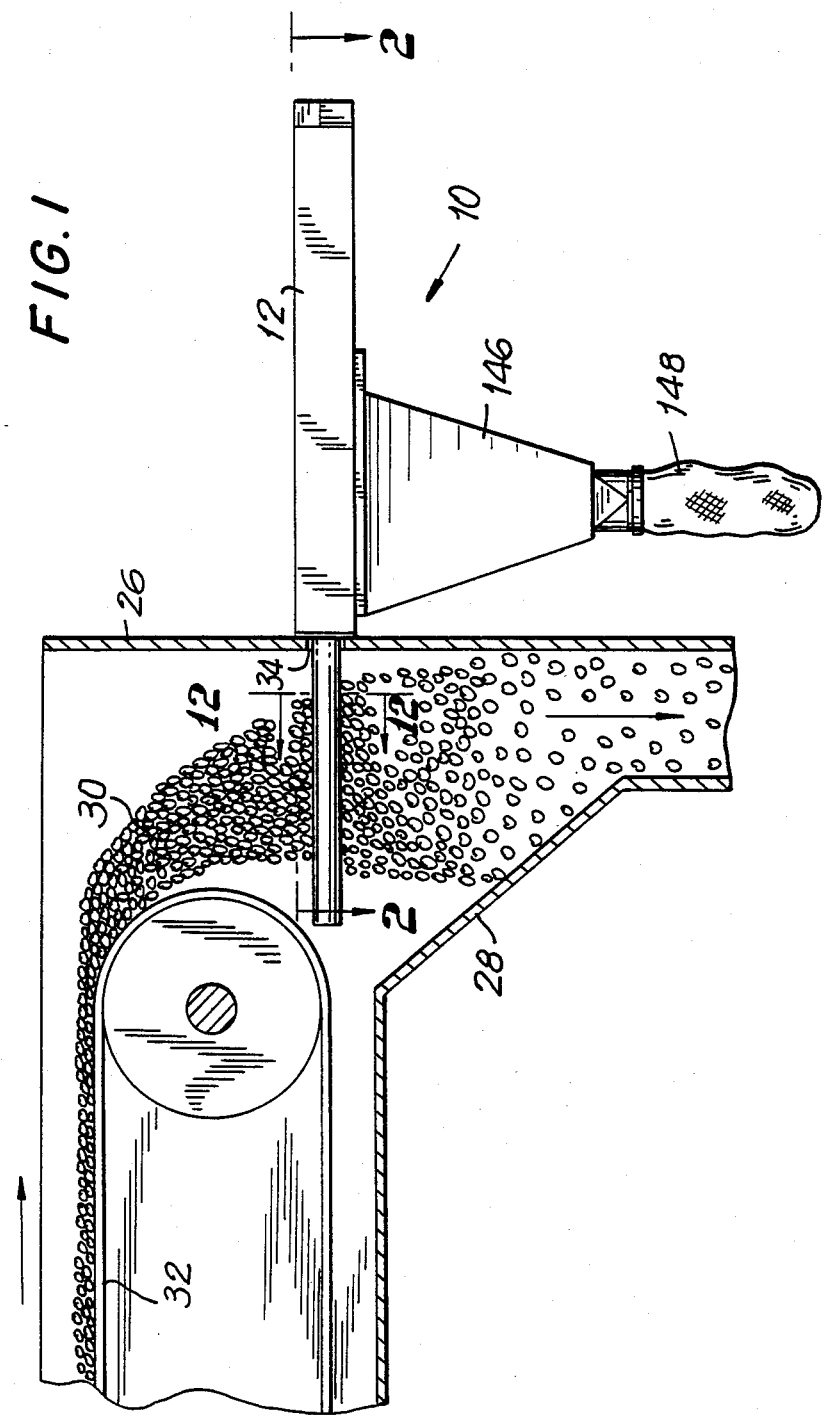

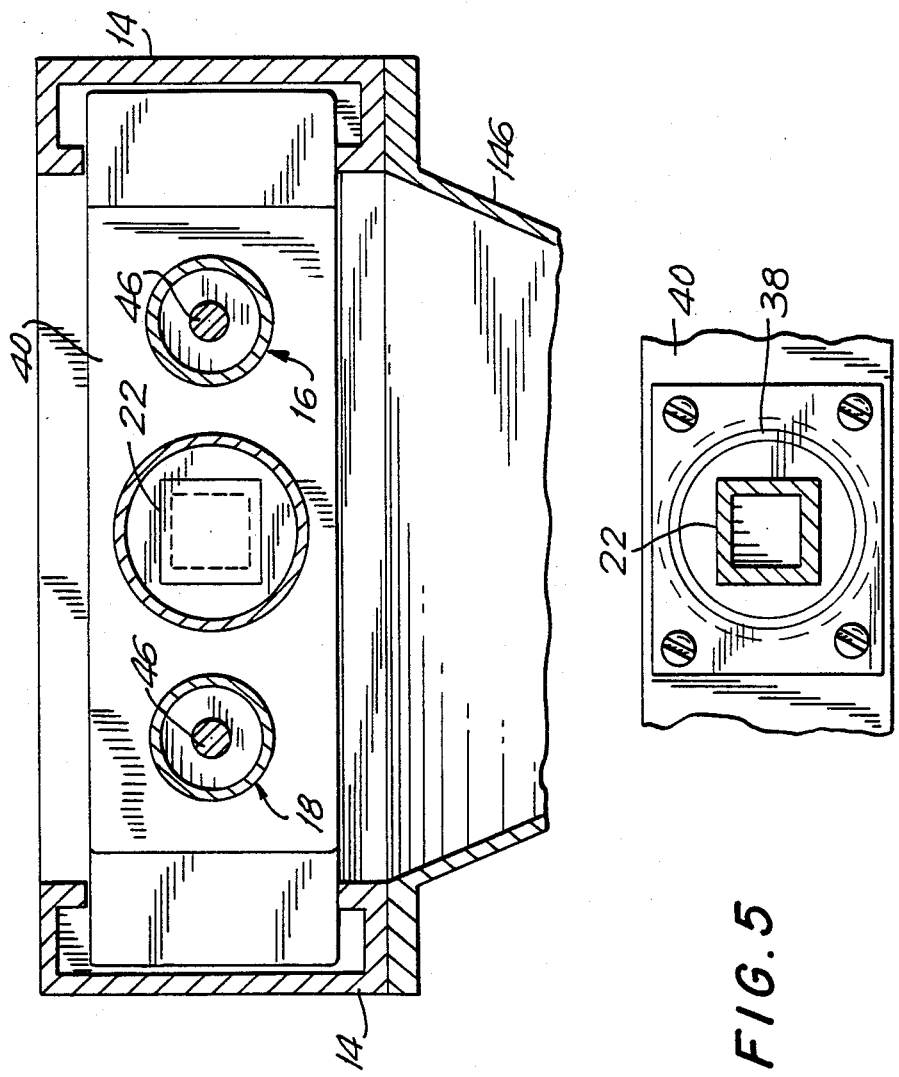

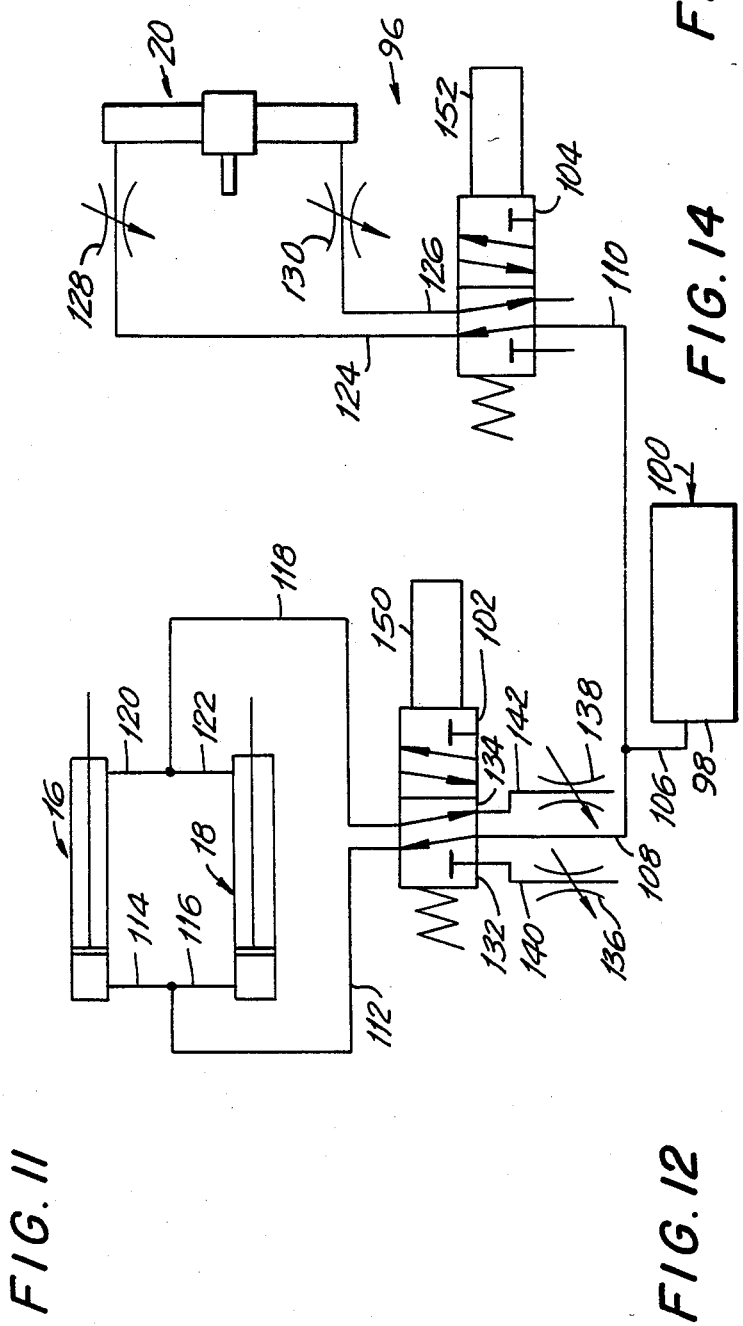

SAMPLER FOR SOLID MATERIALS

BACKGROUND OF THE INVENTION

The prior art related to the extraction of samples of granular or particulate materials, such as wood chips, includes a number of United States Patents, included among which are the following:

U.S. Pat. No. 2,495,944 issued to W. H. Pletta et al shows a coal sampler in which a sample collector is formed of a length of pipe which has a longitudinally extending quarter section removed to provide an arcuate opening. The sample collector is pivotally mounted so that it can be swung from one side of a falling coal stream to the other and back again. While the sample collector is in the stream the sample collector rotates in order to catch a sample of the coal stream. When the sample collector leaves the falling stream, the sample collector rotates to discharge the sample.

U.S. Pat. No. 2,683,373 issued to R. W. Gallup et al shows a grain sampler in which a sample cup is inserted into a stream of falling grain. As the cup is inserted into the stream, its motion is guided by a keyway to turn 180 degrees to face upward to be filled. The cup then retracts, still facing up until it reaches almost the end of its retraction stroke, whereupon it rotates 180 degrees to dump the grain.

U.S. Pat. No. 3,782,200 issued to Maas shows a sampling tube which is transversely mounted in a conveying pipe. Falling material enters the sample tube through an inlet opening. A plunger pulls the material in the sampling tube allowing it to fall through a discharge opening.

U.S. Pat. No. 4,743,155 issued to Carey et al shows an inclined conveyor which includes a chain with a plurality of flights which catch a portion of a falling stream and carry it to a sampling bin.

U.S. Pat. No. 4,574,645 issued to Allen et al shows an inclined tube which is permanently located in a vertical chute. The end of the tube has an opening which allows chip samples to enter the tube. When chip samples are to be taken, the tube is rotated 180 degrees in order to align the opening in the tube with the stream of chips, thereby allowing chips to enter the tube and pass downwardly into a container.

U.S. Pat. No. 4,625,570 issued to Witherspoon et al shows a scoop which fills when a cradle faces upwardly into a flow of material. After retraction of the scoop out of the stream of material, the scoop rotates to dump the sampled material.

Each of the devices described in the above patents is generally complex in construction and is not capable of automatically extracting repeatable and representative samples of wood chips. Thus, despite the various types of devices described in the above patents, the need for a practical wood chip sampler has not been met by the prior art.

OBJECTS OF THE INVENTION

It is an object of the present invention to provide a wood chip sampler which is capable of automatically extracting a repeatable and representative sample from a stream of wood chips.

Another object of the present invention is to provide a wood chip sampler which is capable of reliable operation over an extended period of time.

Another object of the present invention is to provide a wood chip sampler which is capable of collecting both fine and large chips during a normal operating cycle.

Another object of the present invention is to provide a wood chip sampler which automatically seals the wood chip product area when not in use.

Another object of the present invention is to provide a wood chip sampler which cannot be jammed and rendered inoperative as a result of the introduction of an excessively oversize product.

Another object of the present invention is to provide a wood chip sampler which allows excessively oversize product to fall out of the apparatus, thereby preventing lockup.

Still another object of the invention is to provide a wood chip sampler which comprises a relatively small number of component parts which are economical to manufacture, resulting in a relatively low overall cost.

SUMMARY OF THE INVENTION

In accordance with the present invention, there is provided a wood chip sampler which is mounted on the wall of a chute through which there is a flow of wood chips. The wood chip sampler includes a frame which supports a pair of pneumatic cylinders and a pneumatic rotary actuator which are connected to a sampling tube or probe. The probe includes a slot which allows the product being sampled to enter the probe.

Upon actuation of the pneumatic cylinders, the probe is driven into the product flow with the slot in a down or six o'clock position. After the probe is fully extended into the product flow, the rotary actuator turns the probe so that the slot passes through the twelve o'clock position with the slot facing the product flow, thereby allowing the product to fill the probe. As the probe continues to turn until the slot is in the three o'clock position, oversize product is thereby allowed to fall out of the probe and thus prevent lockup of the apparatus. The probe is then retracted into a housing and once fully retracted continues to rotate to its starting position with the slot facing downward allowing the sample to be discharged by gravity into a hopper.

A chip cutter is provided on the frame to shear oversize chips which may project from the slot and would be caught between the slot and the housing. Shock absorbers are provided to cushion the impact once the oversize chip is sheared.

BRIEF DESCRIPTION OF THE DRAWINGS

Additional objects and advantages and a further understanding of the invention may be had by referring to the following specification and drawings in which:

FIG. 1 is a side elevation view of a wood chip sampler, in accordance with the present invention, with the wood chip sampler shown in use;

FIG. 4 is a cross-sectional view taken along the line 4—4 of FIG. 2;

FIG. 5 is a cross-sectional view taken along the line 5—5 of FIG. 2;

FIG. 11 is a schematic drawing of the pneumatic control system of the wood chip sampler of FIG. 1;

FIG. 12 is a cross-sectional view taken along the line 12—12 of FIG. 1;

FIG. 13 is a cross-sectional view taken along the line 13—13 of FIG. 3;

FIG. 14 is a cross-sesctional view similar to FIG. 13 showing a rotated position of the sampling probe;

FIG. 15 is a cross-sectional view taken along the line 15—15 of FIG. 8.

DETAILED DESCRIPTION OF THE PREFERRED EMBODIMENT

Figure 1A:
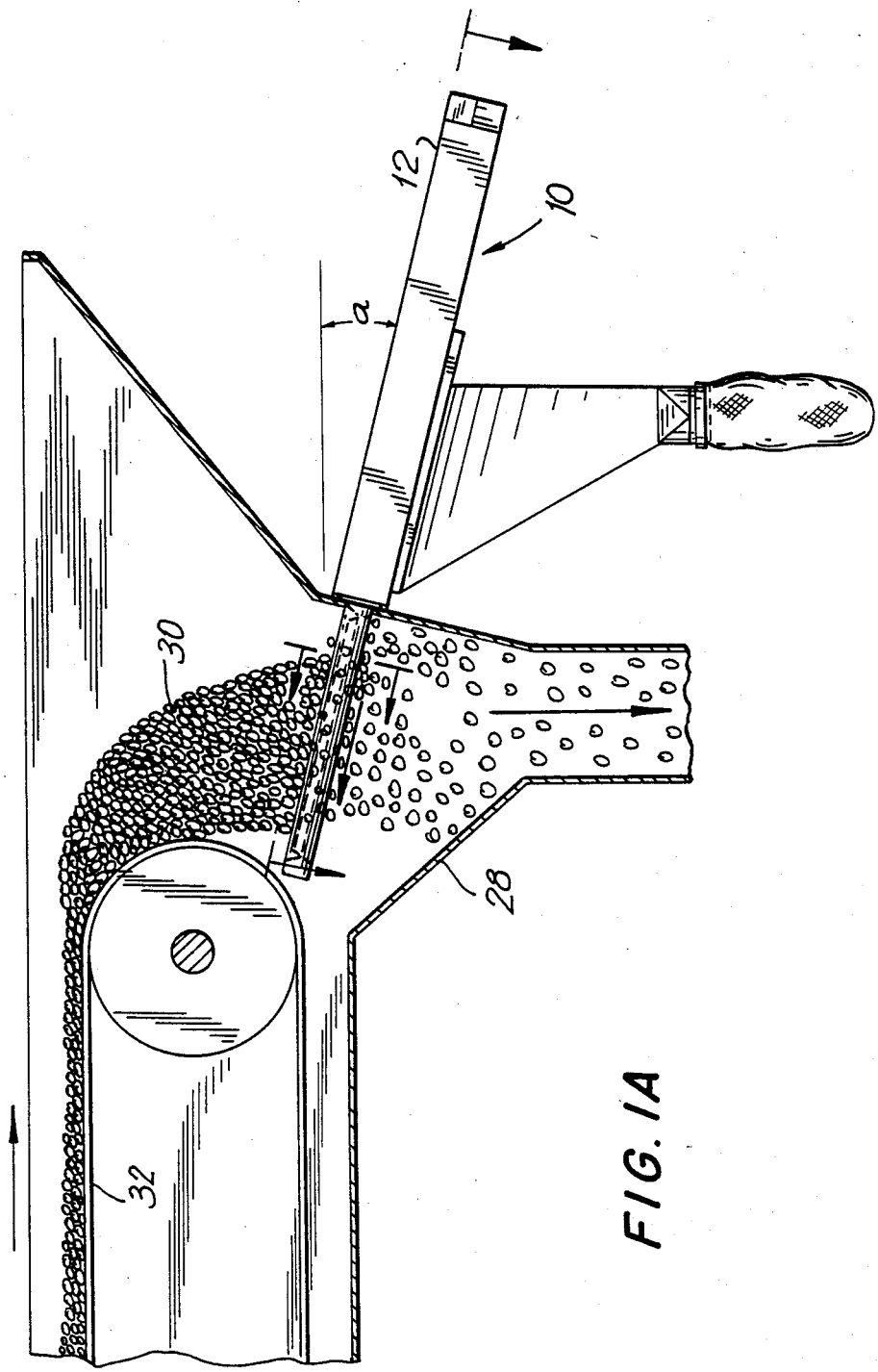
FIG. 1A is a side elevation view similar to FIG. 1 showing an alternative mounting configuration of the wood chip sampler of FIG. 1.
Figure 2:
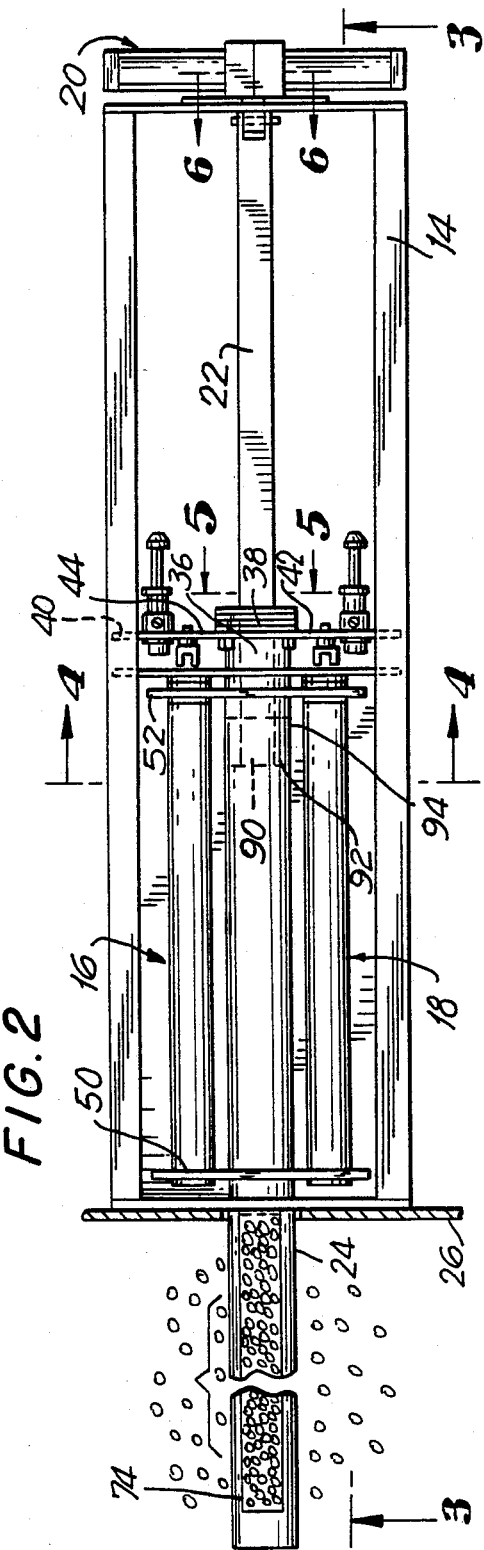
FIG. 2 is a plan view taken along the line 2—2 of FIG. 1.

With reference to the drawings, there is shown in FIGS. 1 and 2 an overall view of a wood chip sampler made in accordance with the present invention which is generally denoted by the reference numeral 10 and which includes: a housing within which there is a support frame 14, which supports a pair of air cylinder assemblies 16, 18, a rotary actuator assembly 20, a drive tube 22, and a sampling probe 24. The wood chip sampler 10, as shown in FIG. 1, is mounted on the side wall 26 of a chute 28 through which there is a flow of wood chip particles 30 which have been delivered by a conveyor belt 32, as is shown in FIGS. 1 and 1A, or by other conventional means such as a spout or a dump pit. The sampling probe 24 projects through an aperture 34 formed in the side wall 26 of the chute 28 and into the flow stream of wood chips 30 for the purpose of extracting a representative product sample in a manner which will be presently described.

Figure 3:
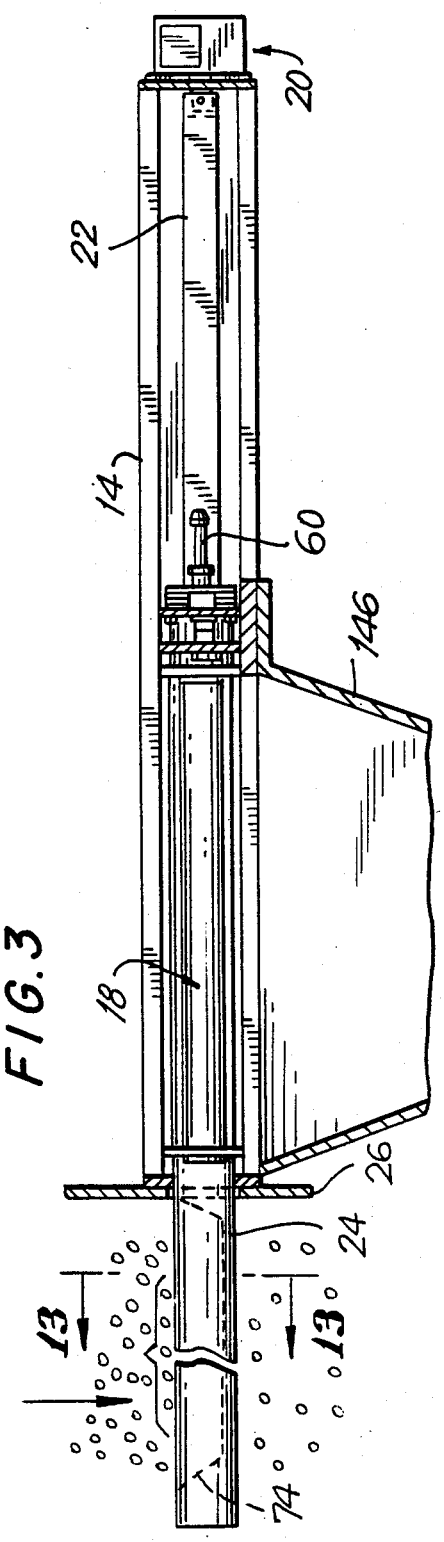
FIG. 3 is a cross-sectional view taken along the line 3—3 of FIG. 2.
Figure 9:
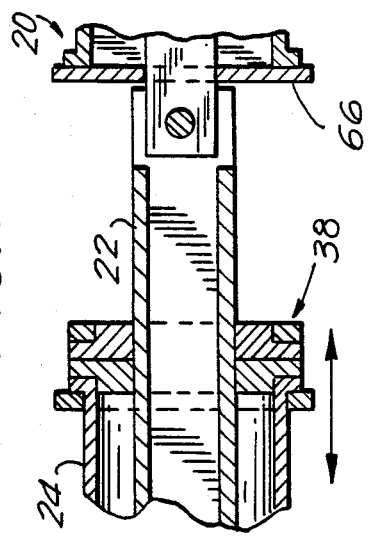
FIG. 9 is a cross-sectional view taken along the line 9—9 of FIG. 7.
Figure 6:
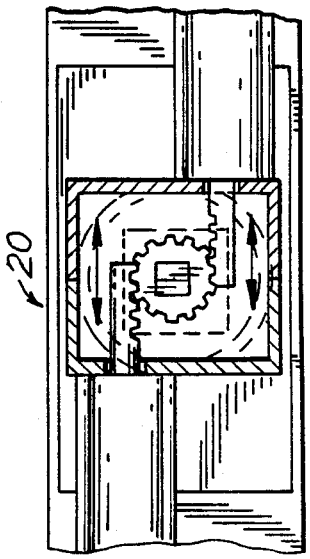
FIG. 6 is a cross-sectional view taken along the line 6—6 of FIG. 2.
Figure 7:
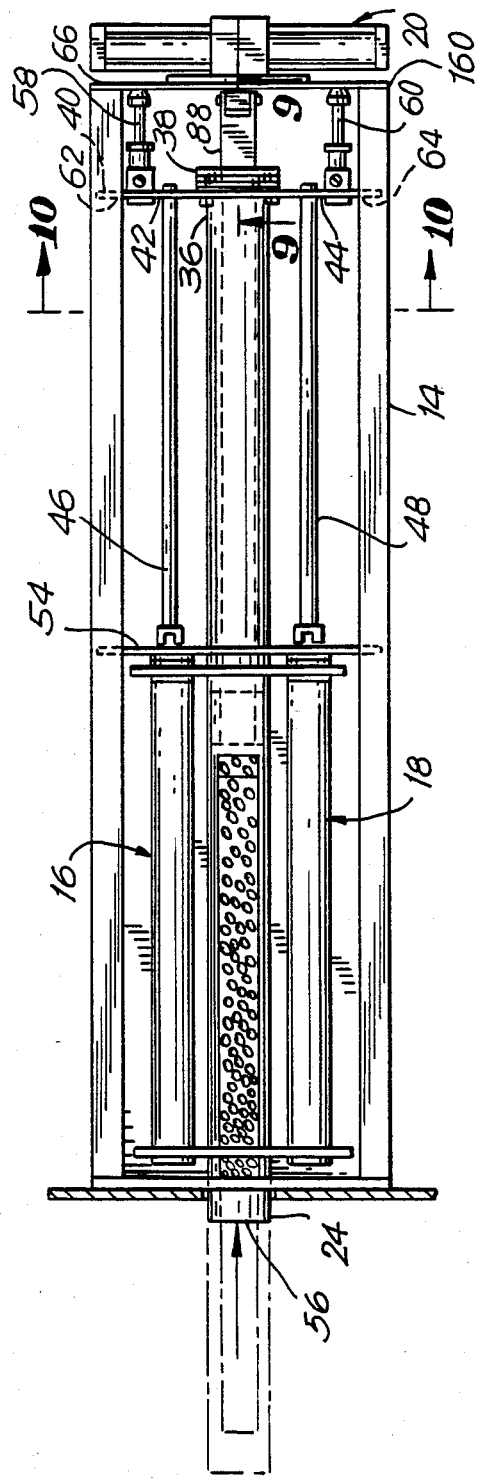
FIG. 7 is a plan view similar to FIG. 2 showing the sampling probe in the retracted position.

As is best shown in FIGS. 2, 3 and 7, the inner end 36 of the sampling probe 24 is mounted in a bearing 38 which is connected to a guide plate 40. Intermediate portions 42, 44 of the guide plate 40 are connected to pistons 46, 48 which are part of the air cylinder assemblies 16, 18. The air cylinder assemblies 16, 18 are connected by strap plates 50, 52.

Figure 10:
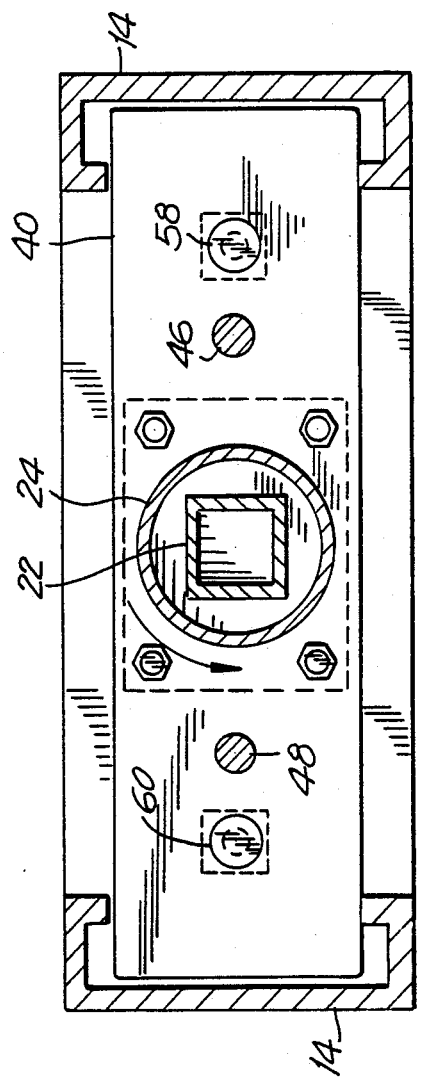
FIG. 10 is a cross-sectional view taken along the line 10—10 of FIG. 7.

The air cylinder assemblies 16, 18 are connected to the support frame 14 by means of an air cylinder support bracket 54. The guide plate 40 is free to translate relative to the support frame 14, as is shown in FIGS. 4 and 10, thereby enabling the end 56 of the sampling probe 24 to project outwardly relative to the support frame 14 and housing 12, as is shown in FIGS. 2 and 3, and also to retract into the support frame 14 and housing 12, as is shown in FIGS. 7 and 8.

The guide plate 40 supports a pair of shock absorbers 58, 60 which are mounted on outer ends 62, 64 of the guide plate 40, as shown in FIGS. 2 and 7. The shock absorbers 58, 60 are capable of contacting the support frame plate 66 shown in FIG. 7 and preventing damaging forces from being transmitted to the operating portions of the apparatus 10.

Figure 8:
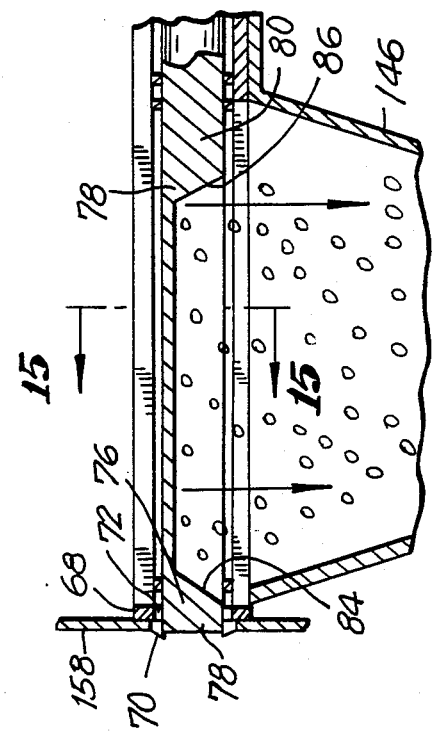
FIG. 8 is a fragmentary cross-sectional view similar to FIG. 3 but showing the sampling probe in a rotated position.

The front plate 68 of the support frame 14 which is best shown in FIG. 8 includes chip cutter ring 70 and a bearing 72 which supports the sampling probe 24.

The sampling probe 24 is formed of tubing from which a section has been removed leaving an open slot 74 as is shown in FIGS. 2, 7 and 12-15. The portions 76, 78 of the sampling probe 24 adjacent to the slot 74 are filled with plug members 78, 80 which have tapered ends 84, 86. The tapered ends 84, 86 facilitate material flow into the slot 74 and to prevent wood chips or other particulate material from being trapped in the sampling probe 24.

The drive tube 22 connects the rotary actuator assembly 20 and the sampling probe 24 and projects into the hollow sampling probe 24 when the sampling probe 24 is in the retracted position shown in FIG. 7. The end 88 of the drive tube 22 is connected to the rotary actuator assembly 20 which in turn is mounted on the support frame 14. The end 90 of the drive tube 22, which is generally square in cross-section, is mounted in a flat drive bearing 92 which is connected to the inside portion 94 of the sampling probe 24, thereby enabling the drive tube 22 to rotate the sampling probe 24 when the sampling probe 24 is in the extended position, FIG. 3, and also when the sampling probe 24 is in the retracted position, FIG. 8.

The operation of the wood chip sampler 10 is controlled by a pneumatic control system 96 which is shown schematically in FIG. 11.

A source of pressurized air, which is not shown, but which is conventional in nature, is connected to filter regulator 98 and enters the filter regulator 98 in the direction shown by the arrow 100 in FIG. 11. The filter regulator 98 is connected to a pair of four-way solenoid valves 102, 104 by means of supply conduits or tubes 106, 108, 110. One of the solenoid valves 102 is connected to the air cylinder assemblies 16, 18 by means of tubes 112, 114, 116, 118, 120, 122. The second solenoid valve 104 is connected to the rotary actuator assembly 20 by means of tubes 124 and 126. The tubes 124, 126 have needle valves 128, 130 mounted thereon and the exhaust ports 132, 134 of the solenoid valve 102 are connected to needle valves 136, 138 by means of tubes 140, 142. The needle valves 128, 130, 132, 134 serve to control the speed of operation of the apparatus 10 by controlling the flow of exhaust air from the pneumatic control system 96.

During operation of the apparatus 10, the sampling probe 24 which is the initial position shown in FIG. 12, with the sample slot 74 in the downward, or six o'clock position, is extended into the product flow by means of the air cylinder assemblies 16, 18 which receive a flow of pressurized air via the tubes 106, 108, 118, 120, 122. After the sampling probe 24 has been fully extended into the product flow, the rotary actuator assembly 20 turns the sampling probe 24 from the 6 o'clock position through the position shown in FIG. 13 with the sample slot 74 in the upward or twelve o'clock position whereby the product flow 30 enters the sample slot 74. The sampling probe 24 continues to rotate until the sample slot 74 is in the three o'clock position shown in FIG. 14. This intermediate, or three o'clock position, allows unusually large particles to fall out of the sampling probe 74 and reenter the product flow stream 30 while retaining a sample of the product 144. Since the probe 24 thus rotates in the product stream from the 6 o'clock, through the 9 o'clock and 12 o'clock positions to the 3 o'clock position after it has been fully inserted therein a more representative product sample is thereby obtained.

The sampling probe 24 is then retracted into the housing 12 by means of the air cylinder assemblies 16, 18 which receive pressurized air via the tubes 106, 108, 112, 114, 116. Once the sampling probe 24 is completely retracted into the housing 12, the sampling probe 24 is again rotated to the initial, or six o'clock position, shown in FIG. 15. This allows the sample material 144 to be discharged from the slot 74 by gravity and to flow into the sample hopper 146 and then into the sample collection bag 148 shown in FIG. 1. The apparatus 10 is then ready for the next operating cycle.

The rotation of the sampling probe 24 is accomplished by means of the rotary actuator 20 which receives pressurized air via the tubes 106, 110, 124, 126 and which drives the sampling probe 24 via the drive tube 22.

The rotation of the sampling probe while in the product stream may be continuous as described above or accomplished in discrete steps, e.g. with a first step being rotation from the 6 o'clock to the 12 o'clock positions and second step from the 12 o'clock to the 3 o'clock positions. By way of further example, the probe may be stepped between various preselected positions located between the 9 o'clock and 3 o'clock positions.

The solenoid portions 150, 152 of the solenoid valves 102, 104 are controlled by a conventional electrical timing circuit which is not shown. The timing circuit allows samples to be taken repetitively in an automatic mode and also allows the apparatus 10 to be operated manually in order to obtain individual samples. When the sampling probe 24 is in the retracted position shown in FIG. 8, the end 56 of the sampling probe 24 is flush with the inner surface 158 of the chute 28, thereby sealing the aperture 34 in the chute 28 and preventing unwanted spillage of the product flow 30.

In the event that an unusually large particle of product is caught and retained by the sampling probe 24, the particle is sheared by the chip cutter 70 which is mounted on the front plate 68 of the support frame 14. The action of shearing this particle normally would result in a shock being transmitted to the apparatus 10. This shock is absorbed by the pair of shock absorbers 58, 60 which are mounted on the guide plate 40 and which make contact with the plate 66 when the guide plate 40 moves toward the end 160 of the housing 12 at high speed. The shock absorbers 58, 60 prevent mechanical damage and prolong the useful life of the apparatus 10.

In FIG. 1 the wood chip sampler 10 has been shown mounted in a generally horizontal position. In FIG. 1A the apparatus 10 has been shown mounted at an angle to the horizontal. While the preferred mounting attitude for the apparatus 10 is horizontal, the apparatus 10 is also capable of operation when mounted at an angle, with the maximum desirable angle as measured by the letter a in FIG. 1A being in the order of forty-five degrees.

Although the apparatus according to the present invention has been described as a wood chip sampler, the application of this apparatus is not limited to the sampling of wood chips but extends to the sampling of a broad range of particulate materials both of uniform and non-uniform sizes and configurations.

While a preferred embodiment of the invention has been shown and described herein, it is obvious that numerous additions, changes and omissions may be made in such embodiment without departing from the spirit and scope of the invention.

What is claimed is:

1. A sampler comprising
a support frame,
probe means mounted on said support frame, with said probe means including a probe cavity portion formed thereon,
translational drive means mounted on said support frame,
first connection means connecting said translational drive means and said probe means for extension of said probe means and retraction of said probe means relative to said support frame,
rotational drive means mounted on said support frame,
second connection means connecting said rotational drive means and said probe means for rotation of said probe means relative to said support frame,
mounting means for mounting said support frame on a product flow chute, and
control system means for control of said extension of said probe means into said product flow chute and into a stream of product flow, followed by rotation of said probe with said probe cavity directed substantially toward said stream of product flow to receive a sample of said product flow, further rotation of said probe means with said probe cavity directed partially away from said product stream, followed by retraction of said probe means away from said product flow chute and followed by further rotation of said probe means to discharge said sample of said product.

2. A sampler according to claim 1 further comprising a product sample hopper mounted on said support frame for the purpose of receiving product samples discharged from said probe means.

3. A sampler according to claim 1, in which said probe means comprises an elongated member.

4. A sampler according to claim 1, in which said cavity portion is defined by a plurality of inclined surfaces.

5. A sampler according to claim 1, in which said probe means includes an outer end and in which said probe means is capable of a first position defined by said cavity portion being in a lowest position, a second position, defined by said cavity portion being in a highest position, and a third position in which said cavity portion is substantially midway between said first and second positions and in which said control system is disposed to extend said probe means relative to said support frame, rotate said probe means from said first position to said second position, further rotate said probe means from said second to said third position, retract said probe means relative to said support frame and further rotate said probe means to said first position.

6. A sampler according to claim 1, in which said translational drive means comprises at least one pneumatic linear actuator.

7. A sampler according to claim 1, in which said rotational drive means comprises a pneumatic rotary actuator.

8. A sampler according to claim 1, in which said control means comprises at least one solenoid valve.

9. A sampler according to claim 1 further comprising shock absorber means disposed between said probe means and said support frame.

10. A sampler according to claim 1 further comprising wood chip cutter means mounted on said support frame.

11. A method for extracting samples from a stream of particulate materials comprising the steps of:

driving a probe member having a cavity portion into a stream of particulate material with said cavity disposed in a first position defined as facing away from the direction of flow of said stream of particulate material;

rotating said probe through a second position defined as said cavity position substantially facing toward the direction of flow of said stream of particulate material;

allowing said cavity to accumulate said particulate material;

rotating said probe to a third position intermediate between said first and second positions;

retracting said probe away from said stream of particulate material; and rotating said probe to said first position thereby allowing material collected in said cavity to discharge under the influence of gravity.

12. A method as defined in claim 11 wherein said rotation of said probe from said first position through said second position to said third position is substantially continuous.

13. A method as defined in claim 11 wherein said second position is substantially at 180° to said first position.

14. A method as defined in claim 11 wherein said third position is substantially at 270° to said first position.

15. A method as defined in claim 11, where in said third position, said cavity portion faces a direction which is substantially perpendicular to the direction of said flow of material.

16. A method as defined in claim 11 wherein the step of rotating said probe to said first position is followed by the step of collecting said material discharged from said cavity.

* * * * *